US006683058B1

(12) United States Patent
Tuszynski

(10) Patent No.: US 6,683,058 B1
(45) Date of Patent: Jan. 27, 2004

(54) METHODS FOR THERAPY OF NEURODEGENERATIVE DISEASE OF THE BRAIN

(75) Inventor: Mark H. Tuszynski, La Jolla, CA (US)

(73) Assignee: Regents of the University of California, Oakland, CA (US)

(*) Notice: Subject to any disclaimer, the term of this patent is extended or adjusted under 35 U.S.C. 154(b) by 0 days.

(21) Appl. No.: 09/620,174

(22) Filed: Jul. 19, 2000

Related U.S. Application Data

(63) Continuation-in-part of application No. 09/060,543, filed on Apr. 15, 1998, now Pat. No. 6,451,306.

(51) Int. Cl.$^7$ .................... A01N 43/04; A01N 63/00; C12N 15/00; C12N 15/63; C07H 21/04

(52) U.S. Cl. .................. 514/44; 435/320.1; 435/455; 424/93.2; 424/93.21; 536/23.5

(58) Field of Search .................. 514/44; 435/320.1, 435/455; 424/93.2, 93.21; 536/23.5

(56) References Cited

U.S. PATENT DOCUMENTS

| | | | |
|---|---|---|---|
| 5,082,670 A | 1/1992 | Gage et al. | 424/520 |
| 5,529,774 A | 6/1996 | Barba et al. | 424/93.21 |
| 5,650,148 A | 7/1997 | Gage et al. | 424/93.2 |
| 5,683,695 A | 11/1997 | Shen et al. | 424/185.1 |
| 5,756,312 A | 5/1998 | Weiner et al. | 435/69.3 |
| 5,762,926 A | 6/1998 | Gage et al. | 424/93.21 |

FOREIGN PATENT DOCUMENTS

| | | |
|---|---|---|
| WO | WO 90/06757 | 6/1990 |
| WO | WO 97/39629 | 10/1997 |
| WO | WO 98/32869 | 7/1998 |
| WO | WO 98/49308 | 11/1998 |
| WO | WO 98/56404 | 12/1998 |
| WO | WO 99/00148 | 1/1999 |
| WO | WO 99/49014 | 9/1999 |

OTHER PUBLICATIONS

Deonarain; Ligand–targeted receptor–mediated vectors for gene delivery, 1998, Exp. Opin. Ther. Patents 8: 53–69.*
Verma et.al.; Gene t herapy—promises, problems and prospects, 1997, Nature, vol. 389: 239–242.*
Eck et.al.;Gene–Based Therapy, 1996, Pharmacological Basis of Therapeutics: 77–101.*
Gorecki; Prospects and problems of gene therapy: an update, 2001, Expert Opin. Emerging Drugs 6(2): 187–198.*
Armelin et al., "Pituitary extracts and steroid hormones in the control of 3T3 cell growth" *Proc. Natl. Acad. Sci.* (1973) 70:2702–6.
Banerji et al., "Expression of a beta–globin gene in enhanced by remote SV40 DNA sequences" *Cell* (1981) 27:299–308.
Benoist et al., "In vivo sequence requirements of the SV40 early promoter region" *Nature* (1981) 290:304–10.

Blesch et al., "Ex vivo gene therapy for Alzheimer's disease and spinal cord injury" *Clinical Neuroscience* (1996) 3:268–274.
Borsani et al., "cDNA sequence of human beta–NGF" *Nucleic Acids Res.* (1990) 18:4020.
Breathnach et al., "Organization and expression of eucaryotic split genes coding for proteins" *Ann. Rev. Biochem.* (1981) 50:349–83.
Chen et al., "Calcium phosphate–mediated gene transfer: a highly efficient transfection system for stably transforming cells with plasmid DNA" *BioTechniques* (1988) 6:632–8.
Chen et al., "High–efficiency transformation of mammalian cells by plasmid DNA" *Mol. Cell. Biol.* (1987) 7:2745–52.
Chua et al., "Tumor necrosis factor–alpha induces mRNA for collagenase and TIMP in human skin fibroblasts" *Connect. Tissue Res.* (1990) 25:161–170.
Conner et al., "Distribution of NGF delivered into the rat CNS by either grafted NGF–secreting fibroblasts, intraparenchymal (IP) injections, or IP–infusions" *Society for Neuroscience* (1997) 23:53 Abstract 29.5.
Corden et al., "Promoter sequences of eukryotic protein–coding genes." *Science* (1980) 209:1406–14.
DePamphilis et al., "Microinjecting DNA into mouse ova to study DNA replication and gene expression and to produce transgenic animals" *BioTechniques* (1988) 6:662–80.
de Wet et al., "The mRNAs for the pro–alpha 1(I) and pro–alpha 2(I) chains of type I procollagen are translated at the same rate in normal human fibroblasts and in fibroblasts from two various of osteogenesis imperfecta with altered steady state ratios of the two mRNAs" *J. Biol. Chem.* (1983) 258:14385–9.
Elias et al., "Regulation of human lung fibroblast collagen production by recombinant interleukin–1, tumor necrosis factor, and interferon–gamma" *Ann. N.Y. Acad. Sci.* (1990) 580:233–244.
Felgner et al., "Cationic liposome mediated transfection" *Proc. West. Pharmacol. Soc.* (1989) 32:115–21.

(List continued on next page.)

Primary Examiner—Shin-Lin Chen
(74) Attorney, Agent, or Firm—Foley & Lardner

(57) ABSTRACT

A specific clinical protocol for use toward therapy of defective, diseased and damaged cholinergic neurons in the mammalian brain, of particular usefulness for treatment of neurodegenerative conditions such as Alzheimer's disease. The protocol is practiced by delivering a definite concentration of recombinant neurotrophin into, or within close proximity of, identified defective, diseased or damaged brain cells. Using a viral vector, the concentration of neurotrophin delivered as part of a neurotrophic composition varies from $10^{10}$ to $10^{15}$ neurotrophin encoding viral particles/ml of composition fluid. Each delivery site receives from 2.5 $\mu$l to 25 $\mu$l of neurotrophic composition, delivered slowly, as in over a period of time ranging upwards of 10 minutes/delivery site. Each delivery site is at, or within 500 $\mu$m of, a targeted cell, and no more than about 10 mm from another delivery site. Stable in situ neurotrophin expression can be achieved for 12 months, or longer.

17 Claims, No Drawings

OTHER PUBLICATIONS

Felgner et al., "Cationic liposome mediated transfection" *Focus.* (1989) 11:21–25.

Felgner et al., "Lipofection: a highly efficient, lipid–mediated DNA–transfection procedure" *Proc. Natl. Acad. Sci.* (1987) 84:7413–7.

Fraley et al., "New generation liposomes: the engineering of an efficient vehicle for intracellular delivery of nucleic acids" *Trends Biochem. Sci.* (1981) 6:77–80.

Fromm et al., "Deletion mapping of DNA regions required for SV40 early region promoter function in vivo" *J. Mol. Appl. Genet.* (1982) 1:457–81.

Gruss et al., "Simian virus 40 tandem repeated sequences as an element of the early promoter" *Proc. Natl. Acad. Sci.* (1981) 78:943–7.

Hefti et al., "Nerve growth factor and Alzheimer's disease" *Ann. Neurol.* (1986) 20:275–81.

Higgins et al., "NGF receptor gene expression is decreased in the nucleus basalis in Alzheimer's disease" *Exp. Neurol.* (1989) 106:222–36.

Horellou et al., "Adenovirus–mediated gene transfer to the central nervous system for Parkinson's Disease" *Experimental Neurobiology* (1997) 144:131–8.

Jolly et al., "Elements in the long terminal repeat of murine retroviruses enhance stable transformation by thymidine kinase gene" *Nucleic Acids Res.* (1983) 11:1855–1872.

Kobayashi et al., "Morphometric study on the CH$ of the nucleus basalis of Meynert in Alzheimer's disease" *Mol. Chem. Neuropathol.* (1991) 15:193–206.

Kordower et al., "The aged monkey basal forebrain: Rescue and sprouting of axotomized basal forebrain neurons after grafts of encapsulated cells secreting human nerve growth factor" *Proc. Natl. Acad. Sci.* (1994) 91:10898–10902.

Lehericy et al., "Heterogeneity and selectivity of the degeneration of cholinergic neurons in the basal forebrain of patients with Alzheimer's disease" *J. Comp. Neurol.* (1993) 330:15–31.

Levivier et al., "Intrastriatal implantation of fibroblasts genetically engineered to produce brain–derived neurotrophic factor prevents degeneration of dopaminergic neurons in a rat model of Parkinson's disease" *The Jo. Of Neuroscience* (1995) 15:7810–20.

Mannino et al., "Liposome mediated gene transfer" *Biotechniques* (1988) 6:682–90.

Maxam et al., "Sequencing end–labeled DNA with base–specific chemical cleavages" *Methods in Enzymology* (1980) 65:499–560.

McCutchan et al., "Enhancement of the infectivity of simian virus 40 deoxy ribonucleic acid with diethylaminoethyldextran" *J. Natl. Cancer Inst.* (1968) 41:351–7.

Messing et al., "A system for shotgun DNA sequencing" *Nucleic Acids Res.* (1981) 9:309–21.

Mesulam et al., "Cholinergic innervation of cortex by the basal forebrain: cytochemistry and cortical connections of the septal area, diagonal band nuclei, nucleus basalis (substantia innominata), and hypothalamus in the rhesus monkey." *J. Comp. Neurol.* (1983) 214:170–197.

Moreau et al., "The SV40 72 base repair repeat has a striking effect on gene expression both in SV40 and other chimeric recombinants" *Nucleic Acids Res.* (1981) 9:6407–6068.

Mufson et al., "Loss of nerve growth factor receptor–containing neurons in Alzheimer's disease: A quantitative analysis across subregions of the basal forebrain" *Exp. Neurol.* (1989) 105:221–32.

Mufson et al., "Nerve growth factor receptor expressing human basal forebrain neurons: pathologic alterations in Alzheimer's and Parkinson's disease" *Prog. Clin. Biol. Res.* (1989) 317:401–14.

Palmer et al., "Genetically modified skin fibroblasts persist long after transplantation but gradually inactivate introduced genes" *Proc. Natl. Acad. Sci* (1991) 88:1330–4.

Potter et al., "Electroporation in biology: methods, applications, and instrumentation" *Anal. Biochem.* (1988) 174:361–73.

Prockop et al., "Heritable diseases of collagen" *N. Eng. J. Med.* (1984) 311:376–86.

Raymon et al., "Application of ex vivo gene therapy in the treatment of Parkinson's disease" *Experimental Neurobiology* (1997) 144:82–91.

Rossi et al., "Identification of a cell–specific transcriptional enhancer in the first intron of the mouse alpha 2 (type I) collagen gene" *Proc. Natl. Acad. Sci.* (1987) 84:5590–4.

Schmidt et al., "Regulation of a collagen promoter by the product of viral mos oncogene" *Nature* (1985) 314:286–9.

Seliger et al., "Gamma interferon regulates long terminal repeat–controlled oncogene expression in transformed mouse fibroblasts at the level of mRNA transcription" *J. Virology* (1988) 62:619–21.

Seliger et al., "Tumor necrosis factor–alpha affects LTR–controlled oncogene expression in transformed mouse fibroblasts at the post–transcriptional level" *J. Immunol.* (1988) 141:2138–44.

Shivaloff et al., "Lines of therapeutic research in Alzheimer's disease" *Psychopharmacology Bulletin* (1996) 32:343–52.

Smith et al., "Age–associated neuronal atrophy occurs in the primate brain and is reversible by growth factor gene therapy" *Proc. Natl. Acad. Sci.* (1999) 96:10893–8.

Smith et al., "Characterization of collagen synthesized by normal and chemically transformed rat liver epithelial cell lines" *Biochem.* (1980) 19:1820–5.

Toneguzzo et al., "Electric field–mediated DNA transfer: transient and stable gene expression in human and mouse lymphoid cells" *Molec. Cell. Biol.* (1986) 6:703–6.

Tuszynski et al., "Gene therapy in the adult primate brain: intraparenchymal grafts of cells genetically modified to produce nerve growth factor prevent cholinergic neuronal degeneration" *Gene Therapy* (1996) 3:305–14.

Tuszynski et al., "Recombinant human nerve growth factor infusions prevent cholinergic neuronal degeneration in the adult primate brain" *Ann. Neurol.* (1991) 30:625–36.

Tuszynski et al., "Somatic gene therapy for nervous system disease" *Ciba Foundation Symposium 196, Growth factors as drugs for neurological and sensory disorders* (1996) 196:85–97.

Tuszynski et al., "The chronically injured spinal cord exhibits responsiveness to NGF delivered locally by gene therapy" *Society for Neuroscience* (1995) 21:1562 Abstract 613.3.

Ullrich et al., "Human beta–nerve growth factor gene sequence highly homologous to that of a mouse" *Nature* (1983) 303:821–5.

Wolff et al., "Expression of retrovirally transduced genes in primary cultures of rat hepatocytes" *Proc. Natl. Acad. Sci.* (1987) 84:3344–8.

Kojima, et al., "Adenovirus–Mediated transduction with human glial cell line–derived neurotrophic factor gene prevents 1–methyl–4–phenyl–1,2,3,6–tetrahydropyridine–induced dopamine depletion in striatum of mouse brain," *Biochemical and Biophysical Research Communications,* 238:569–573 (1997).

Roberts, et al., "Effects of NGF–Secreting Genetically Modified Cell Grafts on Cholinergic Neuronal Morphology and Gocnition in Aged Primates," *Soc. For Neuroscience Abstracts,* 21(2):613.8 (1995).

Yang, et al., "Gene Therapy for Central Nervous System Injury: The Use of Cationic Liposomes: An Invited Review," *Journal of Neurotrauma,* 14(5):281–297 (1997).

Zlokovic, et al., "Cellular and Molecular Neurosurgery: Pathways From Concept to Reality—Part II: Vector Systems and Delivery Methodologies for Gene Therapy of The Central Nervous System," *Neurosurgery,* 40(4):805–813 (1997).

Tuszynski et al., "Targeted intraparenchymal Delivery of Human NGF by Gene Transfer to the Primate Basal Forebrain for 3 Months Does Not Accelerate β–Amyloid Plaque Disposition," *Experimental Neurology,* Article No. EN986956 1–10 (1998).

Grill, et al., "Cellular delivery of neurotrophin–3 promotes corticospinal axonal growth and partial functional recovery after spinal cord injury," *Journal of Neuroscience,* 17(14):5560–5572 (1997).

Tuszynski, et al., "Functional characterization of NGF–secreting cell grafts to the acutely injured spinal cord," *Cell Transplantation,* 6(3):361–368 (1997).

\* cited by examiner

SEQUENCE LISTING

<160> NUMBER OF SEQ ID NOS: 3

<210> SEQ ID NO 1
<211> LENGTH: 3821
<212> TYPE: DNA
<213> ORGANISM: Homo sapiens

<400> SEQUENCE: 1

```
gagctcaaac atagggagat aagtgctgtt ttcacaagat aaaggcaaaa ttcaatccca      60
cgttgccgtt ttgtttctgt tcagtgttcc aaccacagag tggtgctatt gcaaaagata     120
agggtaacca gaaggcacgc tctggaaatt tgctttagga gagagttttta aaggggggttt     180 tcaaaaacaa gatctgattc ctgctctcag aaatcacttc caggagtcag ggccttactc     240
tcagatgcag cagggagaag aagaaagttc agcaacctaa aaatacagtc gacagatggg     300
cagccaaagt catggccacg aagtcaactt ggagaggagc acctacctag tgaatcctaa     360
aagatctcat cctggatgct tccttaacca ggcctatgta cagggcacaa gctcgcagcc     420
agcttacttt ccagtcctga tctttgcttt tgctatccat accaatggta tttctataga     480
aaagaaaaat ctctatttag aaacacggat ttacttagaa gtcacaatat tctagtttaa     540
aaatggctct acatagtaga gaatgatctt tttattctgt cttcttaaaa atacaccttt     600
ctaattcttt ttttcttccc accttcttca ttcagcacct tgccactccc ttggaagcca     660
caacagcgag ctgggggggtc agtccctagt cttagaggga agaaatcttt aggtctgaag     720
tctaaagaaa aacagtaaag gaaaaggcag ttggcggtgc tcaaggtaga ctgtctgaaa     780
gaggtcttct actcagaaaa gggctaaggc tctccctttg ggaaaccaat ccttctgaga     840
aaaagtgcat ctttcaccct ctgctcctgt ctgggtctct ccctcttcct ccctccttcc     900
ctcagtccct cctcccctct ctccacaaag acacagcaca tatttggcaa gattaaggtg     960
tcacctctca tattacaagg cctgttgatt gcaagcaaag acagacccac cagcttagga    1020 caaacccct tggagttgga aataagacaa actctgggat ccccgaaagt cccggcaaaa    1080
tgacgcggcc agccagtgca aggcatctgc agaacaaatc caagtcctaa acgcactgct    1140
tgctgccttt tcttctcctt cctttcttct gatttttcaa gtttgtttgc ccccccttccc    1200 ctcctccctc cagactgcca gggacctggg agctgcctgc agatcagccc gcacatgtat    1260 ttaaccccctt ccctgctgca gcaggagcca accacctctt tccttgcaat cttcaggttc    1320
```

-continued

```
ccagaggacc tggagcttga gaaaagaact ctgccagtgg atctgaaact ggggcctgaa      1380
tccctccttt gaccagggcg agaagctgga ggagggggc aagtgcggga agtgggggag       1440
ggcagggagg cgggccagat gagagggaga aaagcagaac ccgacagagc acgcccaatc      1500
caaaccttca tggtgctgtg tggctgggtg gagggaacga ctcggcagcc tcttctggcc     1560
ctgaggaaga cgtcgatatt ttggcacgag gggagccact gaaggactac cctacccttg     1620
cgagggaccg caggaggtga cgcccctggg cctcggtggg cgcttctggc ggttttcgat     1680
gtggcaaccc ccatcagcca ggataatgat gaggcaggta caatctatct agtacgcagc     1740
ccccagactc ccccctccct tcccacctcc catccaacc cccagctac tctctgcggc       1800 cggttggtcc tgaactggtg ggtgcagttc cgatgtttaa ccaaattctc aagcaatttc     1860
aaggtatttg gattttttga acctgggccc taaccgaaac gcggaacggc ttgcttatta     1920
gacacctcga acgacagcgc agggaggaaa cgggatactc gctgccttc ccagtcgcgc      1980 gtgagtcaaa aggtcctggc aggagatgat gtgaggagcg gctgaagtgg cagggagcaa     2040
gggatgaggg gcttggagcg gaggtccacc acgcaaggac tcgggaagcg ggcaagtggg     2100
caaaactctg cttccgggct ctcgatttct cgttgatcac taagtggtat ttttccccct     2160
tctctcgatg gcaaatgggc gaaatcaaga tgacttaact tggtaaattt agagagaacg     2220
gctcggagca agtgaggtct aacgggcagc taaaattatc tccaaataag agattttgac     2280
cccctccccc tatcctctcc tcgaatgtat ccaccggtgg ggaagtgagc gtcattactt     2340
tcggggcgcc acgacaggtt tgtttgttgc tcgccttttcc tgcttctcgc gctgtccccg     2400
cgtgcagact ggtgggtgct gggcgagtga ttagctgcag ggccccatcc tagttttggaa    2460 ggaagggggtt tagaagttgg aggatgggtg aaatgggagg ctgcgatcca tctccctctc    2520
ccttccacac tcaagctccc gcaaacacgc gcgcgcacac acagcccctc cctagtccct     2580
cggaccaccc gcccccacgc ccctctacct tgacctccct tgaccgccga cacagcgtcc    2640
tgggtgcggg tccccgggag cggggagttc gccggggagc gattgtcctt gggcgtgttc    2700
gtgctgtggg gtgggggggag gagtggcggg tgggcttggt aggggggtggg gagagatctg  2760 gagctggaag ggtctaaggt ttggaggagg agtttacccc tcagacctga tcctcctgac    2820
caaaaaggca ggaaaaggcc ctgatgcctt gtaaagaaaa tcttgaaaga aaaagatca     2880 aaaagaaaaa tttcaagaaa aagaaccact aagaaaggct gaagcacta acatgtaacc    2940 tgttacgata catttaacgt ttcgttttttt cctggatctc taaaagggaa ctcaagggtg   3000 gggggttactg aagaatacta cagatttgga agttttttgtt gctgttgttg tttggtttgg   3060
ttttgttttt caagagggc caggagaaat gacccccttcc ccgccacggg tcccgaagtg    3120
agggcggggg gggggctctg gggcgcgggc gcgcgcggcg cggcgcgggc cggcggggga    3180
gggcggcgcg cgcgcggaagg ggttaaggcg ctgagcgcgg agccatctgg ccgggttggc  3240
tggttataac cgcgcagatt ctgttcacgg gactcagagt tgaagctcct ctcccttccg    3300
aacacgtccg cgcaccgccc cgcgacgcag cccggcgcaa ctactttctt ctctctcctt    3360
tctttcttcc tctccttttt cccctgctgg gtagtggctg cggcggggtg ggggagactt    3420
tgaatgaccg agctcgcgtc cacctttctc ttcatgtcga cgtccctgga aacgccaca     3480 cggatgccat ggttactttt gccacggtaa ggggaggcgg cgggcacctt gggtgggcag    3540
gtttggggat ggggtccac gtgggaggg atttccagt ggactggtgc ggggggcccc      3600
agatccgcat cccgccccac cccatcgcg ccgcgctcac tcactttccc gggcttgtgt     3660
```

```
cttccccaaa gtttgcgctg ggatctgctc aggccgaagc gcaaccgcag ccaccccgct      3720
acacacacac acacacacac acacacacac acacacacac acagacacgg acacccttct      3780
ccacctcctc ccctcttgtc cctcggctgc ccaagaagct t                          3821
```

<210> SEQ ID NO 2
<211> LENGTH: 241
<212> TYPE: PRT
<213> ORGANISM: Homo sapiens

<400> SEQUENCE: 2

```
Met Ser Met Leu Phe Tyr Thr Leu Ile Thr Ala Phe Leu Ile Gly Ile
 1               5                  10                  15

Gln Ala Glu Pro His Ser Glu Ser Asn Val Pro Ala Gly His Thr Ile
            20                  25                  30

Pro Gln Val His Trp Thr Lys Leu Gln His Ser Leu Asp Thr Ala Leu
        35                  40                  45

Arg Arg Ala Arg Ser Ala Pro Ala Ala Ile Ala Ala Arg Val Ala
 50                  55                  60

Gly Gln Thr Arg Asn Ile Thr Val Asp Pro Arg Leu Phe Lys Lys Arg
 65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser Ser His Pro Ile Phe
        115                 120                 125

His Arg Gly Glu Phe Ser Val Cys Asp Ser Val Ser Val Trp Val Gly
    130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
        195                 200                 205

Lys Ala Leu Thr Met Asp Gly Lys Gln Ala Ala Trp Arg Phe Ile Arg
    210                 215                 220

Ile Asp Thr Ala Cys Val Cys Val Leu Ser Arg Lys Ala Val Arg Arg
225                 230                 235                 240

Ala
```

<210> SEQ ID NO 3
<211> LENGTH: 1047
<212> TYPE: DNA
<213> ORGANISM: Homo sapiens

<400> SEQUENCE: 3

```
agagagcgct gggagccgga ggggagcgca gcgagttttg gccagtggtc gtgcagtcca        60 agggctgga tggcatgctg gacccaagct cagctcagcg tccggaccca ataacagttt        120
taccaaggga gcagctttct atcctggcca cactgaggtg catagcgtaa tgtccatgtt       180
gttctacact ctgatcacag cttttctgat cggcatacag gcggaaccac actcagagag       240
caatgtccct gcaggacaca ccatccccca agtccactgg actaaacttc agcattccct      300
```

-continued

```
tgacactgcc cttcgcagag cccgcagcgc cccggcagcg gcgatagctg cacgcgtggc    360
ggggcagacc cgcaacatta ctgtggaccc caggctgttt aaaaagcggc gactccgttc    420
accccgtgtg ctgtttagca cccagcctcc ccgtgaagct gcagacactc aggatctgga    480
cttcgaggtc ggtggtgctg ccccttcaa caggactcac aggagcaagc ggtcatcatc     540
ccatcccatc ttccacaggg gcgaattctc ggtgtgtgac agtgtcagcg tgtgggttgg    600
ggataagacc accgccacag acatcaaggg caaggaggtg atggtgttgg gagaggtgaa    660
cattaacaac agtgtattca aacagtactt ttttgagacc aagtgccggg acccaaatcc    720
cgttgacagc gggtgccggg gcattgactc aaagcactgg aactcatatt gtaccacgac    780
tcacaccttt gtcaaggcgc tgaccatgga tggcaagcag gctgcctggc ggtttatccg    840
gatagatacg gcctgtgtgt gtgtgctcag caggaaggct gtgagaagag cctgacctgc    900
cgacacgctc cctcccctg cccttctac actctcctgg gcccctcct acctcaacct      960 gtaaattatt ttaaattata aggactgcat ggtaatttat agtttataca gtttaaaga   1020 atcattattt attaaatttt tggaagc                                        1047
```

METHODS FOR THERAPY OF NEURODEGENERATIVE DISEASE OF THE BRAIN

RELATED U.S. PATENT APPLICATIONS

This is a continuation-in-part of, and claims the priority of, U.S. patent application, Ser. No. 09/060,543, which was filed on Apr. 15, 1998, now U.S. Pat. No. 6,451,306.

FIELD OF THE INVENTION

The invention relates to methods for treatment of neurodegenerative disease and methods for delivery of therapeutic neurotrophins into the mammalian brain.

HISTORY OF THE RELATED ART

Neurotrophins play a physiological role in the development and regulation of neurons in mammals. In adults, basal forebrain cholinergic neurons, motor neurons and sensory neurons of the CNS retain responsiveness to neurotrophic factors and can regenerate after loss or damage in their presence. For this reason, neurotrophins are considered to have great promise as drugs for the treatment of neurodegenerative conditions such as Alzheimer's Disease (AD), Parkinson's Disease (PD), amyotrophic lateral sclerosis (ALS), peripheral sensory neuropathies and spinal cord injuries.

Clinical trials for the use of neurotrophins in the treatment of AD, ALS and sensory neuropathies are underway. However, the search for a protocol for delivery of neurotrophins to target tissues with minimal side effects (e.g., from diffusion to non-targeted cells or immune reaction to the delivery vehicle) and sufficient penetration of the CNS (e.g., bypassing the blood-brain barrier and achieving chronic delivery of neurotrophin to target cells) has not yet revealed a clear path for clinical administration of neurotrophins. In particular, effective delivery methods and dosing parameters have not yet been identified, although several methods have been proposed. Therefore, although the prospects for therapy of neurodegenerative disease of the brain and CNS are believed to be bright, a successful clinical protocol remains elusive.

SUMMARY OF THE INVENTION

The invention provides a clinically useful protocol for delivery of neurotrophins into the mammalian brain. The invention is particularly useful in treating neurodegenerative conditions in primates, in whom neurotrophins delivered according to the invention stimulate growth of neurons and recovery of neurological function.

More specifically, the invention consists of methods for intraparenchymal delivery of neurotrophins to defective, diseased or damaged cells in the mammalian brain. In one aspect, the invention provides a specific protocol for use in genetically modifying target cholinergic neurons ("target cells") to produce a therapeutic neurotrophin. The genetic modification of target cells is achieved by in vivo transfection of neurons targeted for treatment, or by transfection of cells neighboring these target neurons (neurons or glia), with a recombinant expression vector for expression of the desired neurotrophin in situ.

The location for delivery of individual unit dosages of neurotrophin into the brain is selected for proximity to previously identified defective, diseased or damaged target cells in the brain. To intensify exposure of such target cells to the endogenous growth factors, each delivery site is situated no more than about 500 $\mu$m from a targeted cell and no more than about 10 mm from another delivery site. The total number of sites chosen for delivery of each unit dosage of neurotrophin will vary with the size of the region to be treated.

Optimally, for delivery of neurotrophin using a viral expression vector, each unit dosage of neurotrophin will comprise 2.5 to 25 $\mu$l of an expression vector composition, wherein the composition includes a viral expression vector in a pharmaceutically acceptable fluid ("neurotrophic composition") and provides from $10^{10}$ up to $10^{15}$ NGF expressing viral particles per ml of neurotrophic composition. According to the method, neurotrophic composition is delivered to each delivery site in the brain by injection through a surgical incision, with delivery to be completed within about 5–10 minutes, depending on the volume of neurotrophic composition to be provided.

This targeted, regionally specific protocol for nervous system growth factor delivery avoids limitations imposed by diffusion of substances across the blood-brain barrier and through central nervous system (CNS) parenchyma, while avoiding potential adverse effects of neurotrophic factors delivered intact in a non-directed manner to the CNS.

DETAILED DESCRIPTION OF THE INVENTION

I. Target Tissues for Treatment of Neurodegenerative Disorders According to the Invention The invention identifies and defines the required parameters of a method for successful regeneration of neurons in the brain with neurotrophins, especially the neurons whose loss is associated with neurodegenerative conditions with impairment of cognition such as AD.

The first method parameter defined by the invention is selection of a suitable target tissue. A region of the brain is selected for its retained responsiveness to neurotrophic factors. In humans, CNS neurons which retain responsiveness to neurotrophic factors into adulthood include the cholinergic basal forebrain neurons, the entorhinal cortical neurons, the thalamic neurons, the locus coeruleus neurons, the spinal sensory neurons and the spinal motor neurons. Abnormalities within the cholinergic compartment of this complex network of neurons have been implicated in a number of neurodegenerative disorders, including AD, Parkinson's disease, and amyotrophic lateral sclerosis (ALS, also known as Lou Gehrig's disease). The cholinergic basal forebrain (particularly, the Ch4 region of the basal forebrain) is a particularly suitable target tissue.

Within the primate forebrain, magnocellular neurons Ch1–Ch4 provide cholinergic innervation to the cerebral cortex, thalamus and basolateral nucleus of the amygdala. In subjects with neurodegenerative diseases such as AD, neurons in the Ch4 region (nucleus basalis of Meynert) which have nerve growth factor (NGF) receptors undergo marked atrophy as compared to normal controls (see, e.g., Kobayashi, et al., Mol. Chem. Neuropathol., 15:193–206 (1991)).

In normal subjects, neurotrophins prevent sympathetic and sensory neuronal death during development and prevents cholinergic neuronal degeneration in adult rats and primates (Tuszynski, et al., Gene Therapy, 3:305–314 (1996)). The resulting loss of functioning neurons in this region of the basal forebrain is believed to be causatively linked to the cognitive decline experienced by subjects suffering from neurodegenerative conditions such as AD (Tuszynski, et al., supra and, Lehericy, et al., J. Comp. Neurol., 330:15–31 (1993)).

In human AD, basal forebrain neuronal loss occurs over an intraparenchymal area of approximately 1 cm in diameter. To treat affected neurons over such a large region, treatment with vector composition at upwards of 10 separate in vivo gene vector delivery sites is desirable. However, in treating localized injuries to the basal forebrain, the affected areas of the brain will likely be smaller such that selection of fewer delivery sites (e.g., 5 or fewer) will be sufficient for restoration of a clinically significant number of cholinergic neurons.

Importantly, specific in vivo gene delivery sites are selected so as to cluster in an area of neuronal loss. Such areas may be identified clinically using a number of known techniques, including magnetic resonance imaging (MRI) and biopsy. In humans, non-invasive, in vivo imaging methods such as MRI will be preferred. Once areas of neuronal loss are identified, delivery sites are selected for stereotaxic distribution so each unit dosage of NGF is delivered into the brain at, or within 500 μm from, a targeted cell, and no more than about 10 mm from another delivery site.

II. Dosing Requirements and Delivery Protocol for Treatment of Neurodegenerative Disorders According to the Invention A further parameter defined by the invention is the dosage of neurotrophin to be delivered into the target tissue. In this regard, "unit dosage" refers generally to the concentration of neurotrophin/ml of neurotrophic composition. For viral vectors, the neurotrophin concentration is defined by the number of viral particles/ml of neurotrophic composition. Optimally, for delivery of neurotrophin using a viral expression vector, each unit dosage of neurotrophin will comprise 2.5 to 25 μl of a neurotrophic composition, wherein the composition includes a viral expression vector in a pharmaceutically acceptable fluid and provides from $10^{10}$ up to $10^{15}$ NGF expressing viral particles per ml of neurotrophic composition.

The neurotrophic composition is delivered to each delivery cell site in the target tissue by microinjection, infusion, scrape loading, electroporation or other means suitable to directly deliver the composition directly into the delivery site tissue through a surgical incision. The delivery is accomplished slowly, such as over a period of about 5–10 minutes (depending on the total volume of neurotrophic composition to be delivered).

Those of skill in the art will appreciate that the direct delivery method employed by the invention obviates a limiting risk factor associated with in vivo gene therapy; to wit, the potential for transfection of non-targeted cells with the vector carrying the NGF encoding transgene. In the invention, delivery is direct and the delivery sites are chosen so diffusion of secreted NGF takes place over a controlled and pre-determined region of the brain to optimize contact with targeted neurons, while minimizing contact with non-targeted cells.

Startlingly, in primates, a viral vector (AAV) with an operable neurotrophin encoding transgene has been shown to express human neurotrophin after delivery to the brain and to the CNS for up to 12 months. As such, the invention provides a chronically available source for neurotrophin in the brain.

III. Materials for Use in Practicing the Invention

Materials useful in the methods of the invention include in vivo compatible recombinant expression vectors, pack-aging cell lines, helper cell lines, synthetic in vivo gene therapy vectors, regulatable gene expression systems, encapsulation materials, pharmaceutically acceptable carriers and polynucleotides coding for nervous system growth factors of interest.

A. Neurotrophins

Known nervous system growth factors include nerve growth factor (NGF), brain-derived neurotrophic factor (BDNF), neurotrophin-3 (NT-3), neurotrophin-4/5 (NT-4/5), neurotrophin-6 (NT-6), ciliary neurotrophic factor (CNTF), glial cell line-derived neurotrophic factor (GDNF), the fibroblast growth factor family (FGF's 1–15), leukemia inhibitory factor (LIF), certain members of the insulin-like growth factor family (e.g., IGF-1), the neurturins, persephin, the bone morphogenic proteins (BMPs), the immunophilins, the transforming growth factor (TGF) family of growth factors, the neuregulins, epidermal growth factor (EGF), platelet-derived growth factor (PDGF), and others. NGF and NT-3 in particular have been tested with promising results in clinical trials and animal studies (see, e.g., Hefti and Weiner, Ann Neurol., 20:275–281 (1986); Tuszynki and Gage, Ann. Neurol., 30:625–636 (1991); Tuszynski, et al., Gene Therapy, 3:305–314 (1996) and Blesch and Tuszynski, Clin. Neurosci., 3:268–274 (1996)). Of the known nervous system growth factors, NGF and NT-3 (for treatment of the Ch4 region, as in AD) are preferred for use in the invention.

Human (h) NGF and hNT3 are preferred for use in therapy of human disease according to the invention due to their relatively low immunogenicity as compared to allogenic growth factors. However, other nervous system growth factors are known which may also be suitable for use in the invention with adequate testing of the kind described herein.

Coding polynucleotides for hNGF and hNT3 are known, as are coding sequences for neurotrophins of other mammalian species (e.g., mouse, in which the coding sequence for NGF is highly homologous to the human coding sequence). For example, a cDNA including the coding sequence for hNGF is reported in GenBank at E03015 (Kazuo, et al., Japanese Patent Application No. JP19911175976-A, while the nucleotide sequence of genomic hNGF (with putative amino acid sequence) is reported in GenBank at HSBNGF (Ullrich, Nature, 303:821–825 (1983)) and the mRNA sequence is reported in GenBank at HSBNGFAC (Borsani, et al., Nucleic Acids Res., 18:4020 (1990)). The genomic nucleotide sequence of hNT3 is reported in GenBank at E07844 (Asae, et al., JP Patent Application No. 1993189770-A4). These references are incorporated herein to illustrate knowledge in the art concerning nucleotide and amino acid sequences for use in synthesis of neurotrophins.

B. Recombinant Expression Vectors

The strategy for transferring genes into target cells in vivo includes the following basic steps: (1) selection of an appropriate transgene or transgenes whose expression is correlated with CNS disease or dysfunction; (2) selection and development of suitable and efficient vectors for gene transfer; (3) demonstration that in vivo transduction of target cells and transgene expression occurs stably and efficiently; (4) demonstration that the in vivo gene therapy procedure causes no serious deleterious effects; and (5) demonstration of a desired phenotypic effect in the host animal.

Although other vectors may be used, preferred vectors for use in the methods of the present invention are viral and non-viral vectors. The vector selected should meet the following criteria: 1) the vector must be able to infect targeted cells and thus viral vectors having an appropriate host range must be selected; 2) the transferred gene should be capable of persisting and being expressed in a cell for an extended period of time (without causing cell death) for stable maintenance and expression in the cell; and 3) the vector should do little, if any, damage to target cells.

Because adult mammalian brain cells are non-dividing, the recombinant expression vector chosen must be able to transfect and be expressed in nondividing cells. At present, vectors known to have this capability include DNA viruses such as adenoviruses, adeno-associated virus (AAV), and certain RNA viruses such as HIV-based lentiviruses and feline immunodeficiency virus (FIV). Other vectors with this capability include herpes simplex virus (HSV).

For example, a HIV-based lentiviral vector has recently been developed which, like other retroviruses, can insert a transgene into the nucleus of host cells (enhancing the stability of expression) but, unlike other retroviruses, can make the insertion into the nucleus of non-dividing cells. This lentiviral vector has been shown to stably transfect brain cells after direct injection, and stably express a foreign transgene without detectable pathogenesis from viral proteins (see, Naldini, et al., Science, 272:263–267 (1996), the disclosure of which is incorporated by reference). Following the teachings of the researchers who first constructed the HIV-1 retroviral vector, those of ordinary skill in the art will be able to construct lentiviral vectors suitable for use in the methods of the invention (for more general reference concerning retrovirus construction, see, e.g., Kriegler, Gene Transfer and Expression, A Laboratory Manual, W. Freeman Co. (NY 1990) and Murray, EJ, ed., Methods in Molecular Biology, Vol. 7, Humana Press (NJ 1991)).

Adenoviruses and AAV have been shown to be quite safe for in vivo use and have been shown to result in long-term gene expression in vivo; they are therefore preferred choices for use in the methods of the invention, where safety and long-term expression of nervous system growth encoding transgenes (persisting for longer than necessary to stimulate regrowth of injured or diseased neurons) is necessary. Those of ordinary skill in the art are familiar with the techniques used to construct adenoviral and AAV vectors and can readily employ them to produce vector compositions useful in the claimed invention (for reference, see, e.g., Straus, The Adenovirus, Plenum Press (NY 1984), pp. 451–496; Rosenfeld, et al., Science, 252:431–434 (1991); U.S. Pat. No. 5,707,618 [adenovirus vectors for use in gene therapy]; and U.S. Pat. No. 5,637,456 [method for determining the amount of functionally active adenovirus in a vector stock], the contents of each of which is incorporated herein to illustrate the level of skill in the art).

Lentiviral-based vectors such as HIV and FIV are currently at earlier stages of development but also are attractive candidates for in vivo gene therapy based upon stability of expression in vivo and safety profiles.

Herpesviruses, alpha viruses and pox viruses are also well-characterized virus vectors which may be applied to the methods of the invention. Of these vectors, adeno-associated vectors are an especially attractive choice for their lack of pathogenicity and ability to insert a transgene into a host genome.

Non-viral delivery methods are also an option for use in the methods of the invention. In particular, the plasmid (in a "naked" or lipid-complexed form), lipoplexes (liposome complexed nucleic acids), amino acid polymer complexes with nucleic acids and artificial chromosomes are all non-viral gene delivery agents which are demonstrably able to transduce cells and deliver a foreign transgene. Synthetic in vivo gene therapy vectors are also an option for use in the methods of the invention.

Construction of vectors for recombinant expression of nervous system growth factors for use in the invention may be accomplished using conventional techniques which do not require detailed explanation to one of ordinary skill in the art. For review, however, those of ordinary skill may wish to consult Maniatis et al., in Molecular Cloning: A Laboratory Manual, Cold Spring Harbor Laboratory, (NY 1982).

Briefly, construction of recombinant expression vectors employs standard ligation techniques. For analysis to confirm correct sequences in vectors constructed, the ligation mixtures may be used to transform a host cell and successful transformants selected by antibiotic resistance where appropriate. Vectors from the transformants are prepared, analyzed by restriction and/or sequenced by, for example, the method of Messing, et al., (Nucleic Acids Res., 9:309, 1981), the method of Maxam, et al., (Methods in Enzymology, 65:499, 1980), or other suitable methods which will be known to those skilled in the art. Size separation of cleaved fragments is performed using conventional gel electrophoresis as described, for example, by Maniatis, et al., (Molecular Cloning, pp. 133–134, 1982).

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., Cell 27:299 (1981); Corden et al., Science 209:1406 (1980); and Breathnach and Chambon, Ann. Rev. Biochem. 50:349 (1981)). For retroviruses, control elements involved in the replication of the retroviral genome reside in the long terminal repeat (LTR) (Weiss et al., eds., The molecular biology of tumor viruses: RNA tumor viruses, Cold Spring Harbor Laboratory, (NY 1982)). Moloney murine leukemia virus (MLV) and Rous sarcoma virus (RSV) LTRs contain promoter and enhancer sequences (Jolly et al., Nucleic Acids Res. 11:1855 (1983); Capecchi et al., In: Enhancer and eukaryotic gene expression, Gulzman and Shenk, eds., pp. 101–102, Cold Spring Harbor Laboratories (NY 1991). Other potent promoters include those derived from cytomegalovirus (CMV) and other wild-type viral promoters.

Promoter and enhancer regions of a number of non-viral promoters have also been described (Schmidt et al., Nature 314:285 (1985); Rossi and de Crombrugghe, Proc. Natl. Acad. Sci. USA 84:5590–5594 (1987)). Methods for maintaining and increasing expression of transgenes in quiescent cells include the use of promoters including collagen type I (1 and 2) (Prockop and Kivirikko, N. Eng. J. Med. 311:376 (1984); Smith and Niles, Biochem. 19:1820 (1980); de Wet et al., J. Biol. Chem., 258:14385 (1983)), SV40 and LTR promoters.

In addition to using viral and non-viral promoters to drive transgene expression, an enhancer sequence may be used to increase the level of transgene expression. Enhancers can increase the transcriptional activity not only of their native gene but also of some foreign genes (Armelor, Proc. Natl. Acad. Sci. USA 70:2702 (1973)). For example, in the present invention collagen enhancer sequences are used with the collagen promoter 2(I) to increase transgene expression. In addition, the enhancer element found in SV40 viruses may be used to increase transgene expression. This enhancer sequence consists of a 72 base pair repeat as described by Gruss et al., Proc. Natl. Acad. Sci. USA 78: 943 (1981); Benoist and Chambon, Nature 290:304 (1981), and Fromm and Berg, J. Mol. Appl. Genetics, 1:457 (1982), all of which are incorporated by reference herein. This repeat sequence can increase the transcription of many different viral and cellular genes when it is present in series with various promoters (Moreau et al., Nucleic Acids Res. 9:6047 (1981).

Transgene expression may also be increased for long term stable expression using cytokines to modulate promoter activity. Several cytokines have been reported to modulate the expression of transgene from collagen 2(I) and LTR promoters (Chua et al., connective Tissue Res., 25:161–170 (1990); Elias et al., Annals N.Y. Acad. Sci., 580:233–244 (1990)); Seliger et al., J. Immunol. 141:2138–2144 (1988) and Seliger et al., J. Virology 62:619–621 (1988)). For example, transforming growth factor (TGF), interleukin (IL)-1, and interferon (INF) down regulate the expression of transgenes driven by various promoters such as LTR. Tumor necrosis factor (TNF) and TGF1 up regulate, and may be used to control, expression of transgenes driven by a promoter. Other cytokines that may prove useful include basic fibroblast growth factor (bFGF) and epidermal growth factor (EGF).

Collagen promoter with the collagen enhancer sequence (Coll(E)) can also be used to increase transgene expression by suppressing further any immune response to the vector which may be generated in a treated brain notwithstanding its immune-protected status. In addition, anti-inflammatory agents including steroids, for example dexamethasone, may be administered to the treated host immediately after vector composition delivery and continued, preferably, until any cytokine-mediated inflammatory response subsides. An immunosuppression agent such as cyclosporin may also be administered to reduce the production of interferons, which downregulates LTR promoter and Coll(E) promoter-enhancer, and reduces transgene expression.

C. Pharmaceutical Preparations

To form a neurotrophic composition for use in the invention, neurotrophin encoding expression vectors (including, without limitation, viral and non-viral vectors) may be placed into a pharmaceutically acceptable suspension, solution or emulsion. Suitable mediums include saline and liposomal preparations.

More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like. Further, a composition of neurotrophin transgenes may be lyophilized using means well known in the art, for subsequent reconstitution and use according to the invention.

A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macro molecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of operatively encoding transgenes in plant, yeast and bacterial cells. In order for a liposome to be an efficient gene transfer vehicle, the following characteristics should be present: (1) encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted gene delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

IV. Methods for Delivery of Vector Composition

Following the protocol defined by the invention, direct delivery of a neurotrophic composition may be achieved by means familiar to those of skill in the art, including microinjection through a surgical incision (see, e.g., Capecchi, Cell, 22:479–488 (1980)); electropotation (see, e.g., Andreason and Evans, Biotechniques, 6:650–660 (1988)); infusion, chemical complexation with a targeting molecule or co-precipitant (e.g., liposome, calcium), and microparticle bombardment of the target tissue (Tang, et al., Nature, 356:152–154 (1992)).

V. Animal Models and Clinical Evaluation

In non-human primate subjects (Example III), the process of aging simulates the neurological changes in the brain experienced in aging humans. An non-aged animal model that also mimics loss of cholinergic neurons in, for example, AD, is transection of the fornix pathway connecting the septum from the hippocampus, which causes spontaneous degeneration of the same neurons which degenerate through aging (see, e.g., Example II). In rats and primates, such transections cause retrograde degeneration of cholinergic and non-cholinergic cell bodies in the septal nucleus and nucleus basalis (Ch4 region) of the brain.

These animals are tractable to treatment with neurotrophins, and model clinical responsiveness to such treatment comparable to aged humans (especially the non-human primates, whose brains are most similar in size and structure to humans). Data demonstrating the use and efficacy of the methods of the invention in these animal models are provided in the Examples.

Clinical evaluation and monitoring of treatment can be performed using the in vivo imaging techniques described above as well as through biopsy and histological analysis of treated tissue. In the latter respect, basal forebrain cholinergic neuronal numbers can be quantified in a tissue sample using, for example, anti-neurotrophin antibody (for immunoassay of secreted neurotrophin) or NGF-receptor (p75) and choline acetyltransferase (ChAT) for labeling of neurons. A sample protocol for in vitro histological analysis of treated and control tissue samples is described in the Examples.

The invention having been fully described, examples illustrating its practice are set forth below. These examples should not, however, be considered to limit the scope of the invention, which is defined by the appended claims. Those of ordinary skill in the art will appreciate that while the Examples illustrate an ex vivo application of the invention, the results achieved will be accessible through in vivo delivery of the nervous system growth factor encoding transgenes described, as taught herein, with in vivo gene delivery sites and direct delivery means substituted for the grafting sites and grafting methods discussed in the Examples.

In the examples, the abbreviation "min." refers to minutes, "hrs" and "h" refer to hours, and measurement units (such as "ml") are referred to by standard abbreviations. All printed materials cited are incorporated herein by reference.

EXAMPLE I

ADENO-ASSOCIATED VIRUS VECTOR CONSTRUCTION AND VIRAL PARTICLE PRODUCTION

For adeno-associated viral vector construction, an expression cassette was cloned containing the following elements: 1) cytomegalovirus promoter ($CMV_{ie}$); 2) a multiple cloning site; 3) an internal ribosome entry site followed by the coding sequence for the active, β-sequence of human nerve growth factor (NGF) or the enhanced form of green fluorescent protein (EGFP); and, 4) a SV40 polyadenylation sequence.

The complete cassette was cloned into the vector psub201 (American Type Culture Collection) after XbaI digestion to remove the AAV coding sequences. For NGF expression the coding sequence for human NGF (see, GENBANK Accession No. X52599) was inserted into the multiple cloning site of psub-CXIE resulting in the vector psub-CXIE-NGF. This vector, termed psub-CXIE, was used to prepare control GFP expressing virus particles. Thus, this vector was used for the production of particles coding for NGF and GFP.

Recombinant adeno-associated virus was produced by co-transfection of 18 μg expression plasmid psub-CXIE or psub-CXIE-NGF, 18 μg pXX2 and 54 μg pXX6 per 150 mm plate of subconfluent 293 cells. Transfected cells were harvested 48 h later and adeno-associated virus was purified by Iodixanol density gradient centrifugation and Heparin affinity chromatography. For virus concentration and buffer exchanges Biomax™ 100K filters were used. Aliquots of virus were stored at −80C. The number of viral particles was determined using Southern dot blotting.

EXAMPLE II

IN VIVO GENE TRANSFER IN AN ANIMAL MODEL OF CHOLINERGIC CELL DEATH

Animals received injections of adeno-associated viral (AAV) vector into an in vivo rat model of cholinergic cell death, to determine the extent and parameters of AAV-NGF vector delivery to prevent neuronal degeneration using in vivo gene delivery. To prepare the animal model, adult Fischer 344 rats underwent fornix transections to induce basal forebrain cholinergic neuronal death. NGF-AAV vector (CXIE-NGF) or control, EGFP-AAV vector (CXIE) was injected into the cholinergic basal forebrain at a range of 2.5 to 10 μl of stock vector solution containing from $10^{10}$–$10^{12}$ particles per ml (neurotrophic composition). Particles were injected over a time period of 3–5 min. into the right hemisphere at the following coordinates: AP−0.3; ML−0.5; DV−6 from brain surface. The skin was closed and animals were allowed to survive for 2–4 weeks.

AAV vector delivery induced increasing zones of transfection with increasing concentration and volume of vector particles. Maximal levels of in vivo gene expression were achieved at the highest concentration of vector and highest volume of injection. Over the two week time period of this experiment, persistent in vivo gene expression was demonstrated. Gene expression was primarily manifested in neurons (>90%) as opposed to glia. No adverse effects of the injections were evident.

Thus, vector doses of 2.5 to 10 μl vector stock at a range of $10^{10}$–$10^{12}$ particles per ml were well-tolerated, resulted in optimal vector delivery to the host cholinergic neuronal system, and did not result in adverse events or undesired vector spread beyond the target neuronal nucleus. NGF and enhanced GFP expression were evident for at least two weeks in vivo.

EXAMPLE III

MODEL OF ALZHEIMER'S DISEASE THROUGH AGING IN PRIMATES

Twelve aged and four adult non-aged Macaca mulatta (rhesus) monkeys were experimental subjects. Non-aged animals (n=4, mean age=9.64±1.90 yrs) did not undergo surgical procedures and their intact brains were studied. Aged monkeys were divided into two experimental groups: NGF recipients (n=6, mean age=22.55±0.56 yrs) and control subjects (n=6, mean age=23.51±1.07 yrs). All procedures and animal care adhered strictly to NIH, AAALAC, USDA,

EXAMPLE IV

PREPARATION OF h-NGF SECRETING FIBROBLASTS

To demonstrate responsiveness to NGF, aged monkeys received intraparenchymal grafts of autologous fibroblasts genetically modified to produce and secrete human NGF, as previously described. Briefly, autologous fibroblasts obtained from skin biopsies were genetically modified in vitro to produce and secrete the active portion of human NGF. Transduction procedures were carried out using replication-incompetent retroviral vectors derived from Moloney murine leukemia virus (MLV). Transduced cells were selected by growth in the neomycin analog G418.

Production of biologically active NGF was verified by induction of neurite outgrowth from PC12 cells as described; production of NGF mRNA was determined by Northern blot; and amounts of NGF produced from cells were assayed by NGF ELISA specific for human NGF and sensitive to 5 pg/ml. Optimal NGF-producing bulk clones were amplified to numbers sufficient for in vivo grafting by serial passaging. Cells were harvested by gentle trypsinization for in vivo grafting.

EXAMPLE V

INTRAPARENCHYMAL DELIVERY INTO PRIMATES OF FIBROBLASTS GENETICALLY MODIFIED TO PRODUCE h-NGF

Monkeys underwent pre-operative MRI scans (see, Tuszynski, et al., Gene Therapy, 3:305–314, 1996) to visualize basal forebrain target grafting regions (see, Mesulam et al., J. Comp. Neurol., 214:170–197, 1983). After generating stereotaxic grafting coordinates from NRI scans, each monkey received intraparenchyrnal grafts of autologous NGF-secreting fibroblasts.

Stereotactic coordinates for surgery were generated from magnetic resonance images (MR) of the brain of each subject. The rostral and caudal boundaries of Ch4 were identified on each subject's MR scan, making reference to primate histological brain sections and to standard primate brain atlases. The total rostral-caudal distance of Ch4 was measured on the MR scan, and five graft injection sites were chosen that were equally distributed over this rostral-caudal distance.

The sites for desired ventral-dorsal (VD) and medial-lateral (ML) injections were chosen such that cell grafts were deposited just dorsal to the desired target at each coordinate (within 500 um), and exactly centered in the mediolateral (ML) plane at the maximal density of cholinergic neuronal somata (estimated by review of histological sections at the corresponding AP level). Thus, five grafts were deposited on each side of the Ch4 region per subject, or ten total grafts per subject. Real-time coordinates for in vivo injections were calculated from calibration scales on the MR image. Subjects underwent surgical grafting in the same stereotaxic apparatus that MR scans were performed in.

To place the grafts, animals were placed into a primate stereotaxic apparatus and a midline scalp incision was used to expose the skull. The AP and ML stereotaxic coordinates for the BFC system were used to define the margins of the craniotomy site. Following craniotomy, a ML zero reference point was obtained by measuring the midpoint of the superior sagittal sinus. The dura was incised and reflected to expose the pial surface. The pial surface at each injection site was used as a VD zero reference point for that injection site.

Using the zero reference points obtained in the AP, ML, and VD planes and the stereotaxic injection coordinates calculated from that animal's MR scan, 5 ul of cells were injected into each of 5 sites over the rostral-caudal extent of the Ch4 targeted region bilaterally (10 grafts total per animal) using 25-gauge Hamilton syringe. Grafts were generally targeted to a position slightly dorsal to but within 500 um of Ch4 nuclei. The injection rate was controlled at 5 ul/min. Cells were injected at a concentration of $1.0 \times 10^5$ cells/ul (for a total of 10 million grafted cells per animal), a concentration that optimally maintains cells in suspension without clumping but sufficiently concentrated to maximize number of surviving cells in vivo. Monkeys survived for three months before sacrifice.

Some control aged subjects received intraparenchymal grafts as noted above. These grafted cells consisted either of autologous fibroblasts transduced to express the reporter gene beta-galactosidase (n=6 monkeys). Beta-gal production was assessed in vitro using a specific anti-beta-gal antibody. Cells were grafted into intraparenchymal sites in numbers identical to those described above for NGF graft recipients.

For all surgical procedures, primates were preanesthetized with 25 mg/kg ketamine IM. They were then anesthetized with isoflurane administered by endotracheal intubation. Post-operatively animals were closely monitored, and received supportive care and appropriate analgesics when indicated. Animals were placed in the same primate stereotaxic apparatus (Crist Instruments) that was used to perform MRI scans. A midline scalp incision exposed the skull. A 2.5×5 cm sagittally oriented craniotomy was performed on each side of the hemicranium, and the dura was incised and reflected to expose sites for stereotaxically guided cell injections. Ten ul of cells were injected into each site through a 25 ga. Hamilton syringe at a rate of 1 ul/minute. Postoperatively, all experimental subjects were observed closely for signs of discomfort or toxicity. After a three-month survival period, animals were perfused transcardially for one hour with a 4% solution of paraformaldehyde in 0.1M phosphate buffer followed by 5% sucrose solution in the same buffer for 20 minutes. The brain was stereotaxically blocked in the coronal plane.

EXAMPLE VI

REVERSAL OF AGE-RELATED p75 EXPRESSION LOSS

In AD brains, NGF accumulates in regions of basal forebrain cholinergic neurons and is decreased in the basal forebrain, leading to the hypothesis that insufficient retrograde transport of NGF promotes the degeneration of basal forebrain cholinergic neurons observed in AD. In humans, basal forebrain cholinergic neuron dysfunction has been closely linked with age-related cognitive and memory impairment.

In the mammalian brain, it is believed that the p75 receptor collaborates with the TrkA receptor to form high-affinity binding sites for NGF. Although activation of TrkA is sufficient for NGF to rescue axotomized cholinergic neurons, disruption of NGF binding to p75 reduces NGF binding to TrkA. Hence, co-expression of the two receptors can lead to greater responsiveness to NGF. Conversely, loss of expression may lead to decreased responsiveness to NGF. Expression of both p75 and TrkA is regulated by NGF, so that a loss of NGF signalling further reduces the amount of both p75 and TrkA. Combined with a loss of expression of TrkA in AD brains, leading to reduced amounts of TrkA protein in both the basal forebrain and the cortex, decreased p75 expression may contribute to a decline in retrograde NGF, signalling. Thus, p75 expression is a marker for NGF binding, basal forebrain cholinergic neuron dysfunction and cognitive impairment.

To determine the effect of the method of the invention on p75 expression in treated primate brains, monkeys were treated as described in Example III. Each subject was then deeply anesthetized with ketamine and nembutal and perfused transcardially for 1 hour with a 4% solution of paraformaldehyde in 0.1M phosphate buffer, followed by 5% sucrose solution in the same buffer for 20 min. The brains were then stereotaxically blocked in the coronal plane to obtain a single block containing the full AP extent of Ch4.

Coronal sections were cut on a freezing microtome set at 40 um. Every sixth section was processed for p75 immunoreactivity. Briefly, sections were washed thoroughly in Tris-buffered saline (TBS) and endogenous peroxidases were quenched by incubating in a 0.6% hydrogen peroxide solution. Sections were rinsed in TBS and then blocked using 5% donkey serum with 0.5% Triton X-100 in TBS (TBS++). Incubation in primary antibody (monoclonal diluted 1:100 in TBS++) occurred for 24 hours at room temperature. Sections were rinsed in TBS++, incubated in secondary antibody (biotinylated donkey-anti-mouse diluted 1:500 in TBS++) for 1 hour, rinsed again in TBS++, and then incubated for 90 minutes using a Vector ABC kit. p75-labeled neurons were then visualized using diaminobenzidine (DAB) as a chromogen. Sections were then mounted and coverslipped.

p75-labeled neurons were quantified in Ch4i neurons using stereological procedures. Ch4i was targeted in this study since this region is the principal site of origin of cholinergic projections to cortical regions that modulate memory.

Ch4 can be divided topographically into three subdivisions, the anterior (Ch4a), intermediate (Ch4i), and posterior (Ch4p). The anterior subdivision is further divided into medial (Ch4am) and lateral (Ch4al) sectors, which are divided by a vascular structure or rarefication in the density of neurons. However, as Ch4a travels in the posterior direction toward Ch4i, the division between Ch4am and Ch4al becomes less distinct and in some disappears. In this region the ansa peduncularis, the characteristic structure of Ch4i, begins to make its appearance. The ansa peduncularis divides Ch4i into ventral (Ch4iv) and dorsal (Ch4id) components. There is typically also a portion of the anterior commissure present over the lateral portion of Ch4id at this level that serves as the anterior boundary of Ch4i. At the posterior boundary of Ch4i, Ch4iv and Ch4id merge into a single nucleus embedded in the intersection of the globus pallidus, putamen, and optic tract.

Stereological counts were performed on every sixth section through the entire extent of Ch4i. The NeuroZoom™ stereology computer program running on an Apple Macintosh PowerPC™ and connected to a Javelin™ video camera mounted on an Olympus VanoX™ HBT-3 microscope was used to conduct stereology by the well-known West optical dissector method. Briefly, the region of interest (Ch4i) was outlined in NeuroZoom using a 1X objective. Specific stereology parameters were then set in NeuroZoom as follows:

Fraction (percent of area): 5%
Counting frame size: x=66.46 um, y=53.73 um
Section thickness: 40 um These parameters were adjusted to minimize the coefficient of error of the estimate (CE(P)) while maximizing the efficiency of sampling.

The NeuroZoom program controlled movement from one counting frame to the next by moving a Ludl motorized stage mounted on the microscope. Ch4i neurons were counted using a 60X high numerical aperture (1.40) oil objective. Cells were marked to be included in the count if they met the following criteria: 1) they were p75-labeled; 2) the soma was within the counting frame (or touching the inclusion boundary) but did not touch the exclusion boundary; 3) a clearly visible nucleus was present; and 4) the nucleus was best in focus within the inclusion volume (i.e., the top 12.5% and bottom 12.5% were excluded, and the nucleus was not in focus in either of these exclusion volumes). Multiple group comparisons were made by analysis of variance (ANOVA) with post-hoc analysis using Fisher's least squares difference.

The number of p75-labeled Ch4i neurons was compared between four groups of rhesus monkeys, two of which were unoperated and two of which received intraparenchymal grafts of genetically-modified fibroblasts. Young monkeys (mean age=9.375±1.058) constituted one of the unoperated groups, while aged monkeys (mean age=25.139±2.455) comprised the other unoperated group. Of the two aged groups which received grafts to the basal forebrain, one (mean age=22.639±0.463) received grafts of cells modified to produce and secrete NGF, and the other (mean age=23.321±0.927) received grafts of cells modified to produce and secrete beta-gal.

There were significantly fewer p75-labeled neurons in Ch4i from unoperated aged monkeys than from unoperated young monkeys (p<0.01). The mean number of p75-labeled Ch4i neurons from NGF-grafted aged monkeys was significantly greater than from control-grafted aged monkeys (p<0.04). Further, there number of p75-labeled Ch4i neurons in NGF-grafted aged monkeys did not differ from numbers in unoperated young monkey brains (p=0.1288).

These results demonstrate that there is spontaneous loss of expression of the low-affinity neurotrophin receptor (p75) in cholinergic neurons in the basal forebrain, and that re-expression of p75 can be induced by intraparenchmal delivery of NGF.

EXAMPLE VII

HISTOLOGY CONFIRMING IN VIVO UPTAKE OF TRANSGENE, EXPRESSION OF NGF AND LACK OF BETA-AMYLOID INDUCTION

Sections of brain tissue after humane sacrifice of the test animals were cut at 40 um intervals on a freezing microtome. Every sixth section was processed for Nissl stain or hematoxylin and eosin. Immunocytochemical labeling against amyloid was performed using an amyloid-specific monoclonal antibody (anti-A4). Sections lacking primary antibody were processed to verify specificity of labeling. A representative section per subject was quantified from each of the following regions: temporal, frontal, cingulate, insular, parietal and occipital cortices; amygdala and hippocampus; and the intermediate division of the Ch4 region (Nucleus Basalis of Meynert). Sampled sections from each subject were closely matched in region and size. The total number of amyloid plaques per region was quantified and recorded. Observers were blinded to the identity of the tissue being quantified.

All grafted subjects showed surviving cell grafts within 500 um of each grafting site. There was no qualitative difference in fibroblast morphology and overall graft size between NGF- and control-graft recipients. Grafts were most frequently located adjacent to the intermediate division of the Ch4 region of the basal forebrain, but in all cases included at least one graft located within the anterior and posterior divisions of the Ch4 region.

No amyloid plaques at all were detected in adult, non-aged primate tissue. In contrast, control aged monkeys showed a significant increase in amyloid immunolabeling in the frontal, temporal insular and cingulate cortices and amygdala, and extremely small increases in the parietal cortex and hippocampus relative to non-aged monkeys. No plaques at all were present in the cholinergic basal forebrain in any group.

In aged control animals, plaques typically showed a dense central core and a less dense surrounding halo of immun-reactive deposition product, an appearance typical of "mature" plaques observed in AD. This immunolabeling pattern is consistent with previous reports in aged primate brain. However, no increase in amyloid labeling was observed in the aged, NGF-grafted brains, indicating that three months of intraparenchymal NGF delivery does not increase beta-amyloid plaque deposition in the aged primate brain. Thus, the benefits of NGF grafting in the brains of primates exhibiting AD symptoms can be acheived without risk of stimulating amyloid deposition in response to the graft trauma.

Initially, group differences were statistically determined by analysis of variance, with post-hoc analysis utilizing Fisher's least square difference. However, since non-aged adult monkeys showed no amyloid plaques, comparisons between NGF-treated and control aged monkeys were made using unpaired two-way student's t-test.

What is claimed is:

1. A method for delivery of a therapeutic neurotrophin to one or more defective, diseased or damaged cholinergic neurons in the mammalian brain, the method comprising directly delivering a neurotrophic composition, comprising a neurotrophin encoding transgene, into one or more delivery sites within a region of the brain containing targeted neurons, whereby the transgene is expressed in, or within 500 μm from, a targeted cell, and no more than about 10 mm from another delivery site; and wherein contact between the targeted cell and the neurotrophin ameliorates the defect, disease or damage.

2. The method according to claim 1, wherein the transgene is expressed by a viral expression vector.

3. The method according to claim 2, wherein the viral expression vector is an adenovirus.

4. The method according to claim 2, wherein the viral expression vector is an adeno-associated virus.

5. The method according to claim 2, wherein the viral expression vector is a lentivirus.

6. The method according to claim 2, wherein the viral expression vector is HIV-1.

7. The method according to claim 2, wherein the neurotrophic composition is a fluid having a concentration of neurotrophin encoding viral particles in the range from $10^{10}$ to $10^{15}$ particles per ml of neurotrophic composition.

8. The method according to claim 7, wherein from 2.5 μl to 25 μl of the neurotrophic composition is delivered to each delivery site.

9. The method according to claim 8, wherein delivery to each delivery site is accomplished over a period of time greater than or equal to 3 minutes.

10. The method according to claim 9, wherein delivery to each delivery site is accomplished over a period of time less than or equal to 10 minutes.

11. The method according to claim 1 wherein the treated mammal is a human and the transgene encodes a human neurotrophin.

12. The method according to claim 11 wherein the neurotrophin is human beta nerve growth factor (β-NGF).

13. The method according to claim 11 wherein the neurotrophin is human neurotrophin 3 (NT-3).

14. The method according to claim 1 wherein the delivery sites are intraparenchymal.

15. The method according to claim 1 wherein the delivery sites are within the Ch4 region of the cholinergic basal forebrain.

16. The method according to claim 1 wherein the transgene is expressed by a non-viral expression vector.

17. The method according to claim 1 wherein the ameliorated disease is Alzheimer's disease.

* * * * *